United States Patent [19]

Sioufi

[11] Patent Number: 5,409,489
[45] Date of Patent: Apr. 25, 1995

[54] SURGICAL INSTRUMENT FOR CONE-SHAPED SUB-TROCHANTERIC ROTATIONAL OSTEOTOMY

[76] Inventor: Georges Sioufi, 2300 Cote Vertu, Saint-Laurent, Quebec, Canada, H4R 1P1

[21] Appl. No.: 3,507

[22] Filed: Jan. 12, 1993

[51] Int. Cl.$^6$ .......................... A61B 17/00; A61F 2/32
[52] U.S. Cl. ......................... 606/80; 606/86; 606/87
[58] Field of Search ...................... 606/61, 62, 79–80, 606/86, 87, 88, 96, 97, 98, 102, 104

[56] References Cited

U.S. PATENT DOCUMENTS

| | | | |
|---|---|---|---|
| 2,301,500 | 11/1942 | Anderson | 606/96 |
| 2,697,433 | 12/1954 | Zehnder | 606/96 |
| 5,108,396 | 4/1992 | Lackey | 606/87 |
| 5,163,940 | 11/1992 | Bourque | 606/88 |
| 5,228,459 | 7/1993 | Caspari | 606/88 |

OTHER PUBLICATIONS

Marvin E. Steinberg, "The hip and its disorders", 1991, W. Saunders Co., pp. 710 to 723 and 732 to 734.
Evarts, "Surgery of the musculoskeletal system", 2nd edition, pp. 2786 to 2791 and 2806 to 2829.
Jacques Arlet, "Non traumatic a vascular necrosis of the femoral head", C.O.R.R., Apr. 1992, pp. 12 to 19.
Rennie & Cruess, "Adult orthopedies", vol. II, pp. 1222 to 1227 1235 to 1241 and 1253.
Patrick Kinnard et al, "The borden and gearen modification . . . ", C.O.R.R., Jun. 1990, pp. 194 to 197.
R. Eyb et al, "The transtrochanteric anterior rotational ostrotomy of surioka", Arch. Orthop. Trauma Surg. (1987), 106, pp. 161 to 167.
Y. Sugioka, "Transtrochanteric Rotational Osteotomy . . . ", C.O.R.R. Apr. 1984, pp. 12 to 23.
Lester S. Borden et al, "Transtrochanteric Rotational Osteotomy" Orthopeadic Review, vol. XII, No. 5, May 1983.
S. M. T. Tooke et al, "Results of Transtrochanteric Rotational Osteotomy . . . ", C.O.R.R., Nov. 1987, pp. 150 to 157.
James R. Gafe et al' "Complications after cuneiform osteomoty . . . ", J.B.J.S. vol. 60A, 1978, pp. 157 to 165.
Campbell's "Operation Orthopaedics", 8th edition, pp. 203 to 2045.
Campbeel's "Operative Orthopeadics", 7th edition, pp. 1054 to 1056 and 1412.

*Primary Examiner*—Michael A. Brown
*Attorney, Agent, or Firm*—ROBIC

[57] ABSTRACT

A surgical instrument and kit including it, for use to carry out a cone-shaped sub trochanteric rotational osteotomy. The instrument has a guide that is fixed to a cervical screw which has been previously inserted into the femoral head along the axis of the cone to be cut. A drill bit driven in rotation about its own axis passes through the guide in an oblique hole extending at an angle equal to half the angle of the cone to be cut. The drill bit penetrates the lateral wall of the femur as close as possible to the cervical screw. Cutting of the cone is achieved by lateral displacement of the drill bit in a circular motion, which is progressively enlarged as the bit moves forward. In addition to the instrument, the kit contains a chisel with cutting wings, which is insertable in the cervical screw to allow the wings to make slits in the bone. Once the bone is cut and the guide and drill bit have been removed, the ill weight-bearing zone of the patient's femoral head is rotated and replaced by a healthy zone of the femoral head. This kit also has a compression plate which is insertable on the cervical screw and simultaneously in the slits done by the cutting wings of the chisel. This compression plate is used to fasten the femoral head to the femur in its new position.

28 Claims, 8 Drawing Sheets

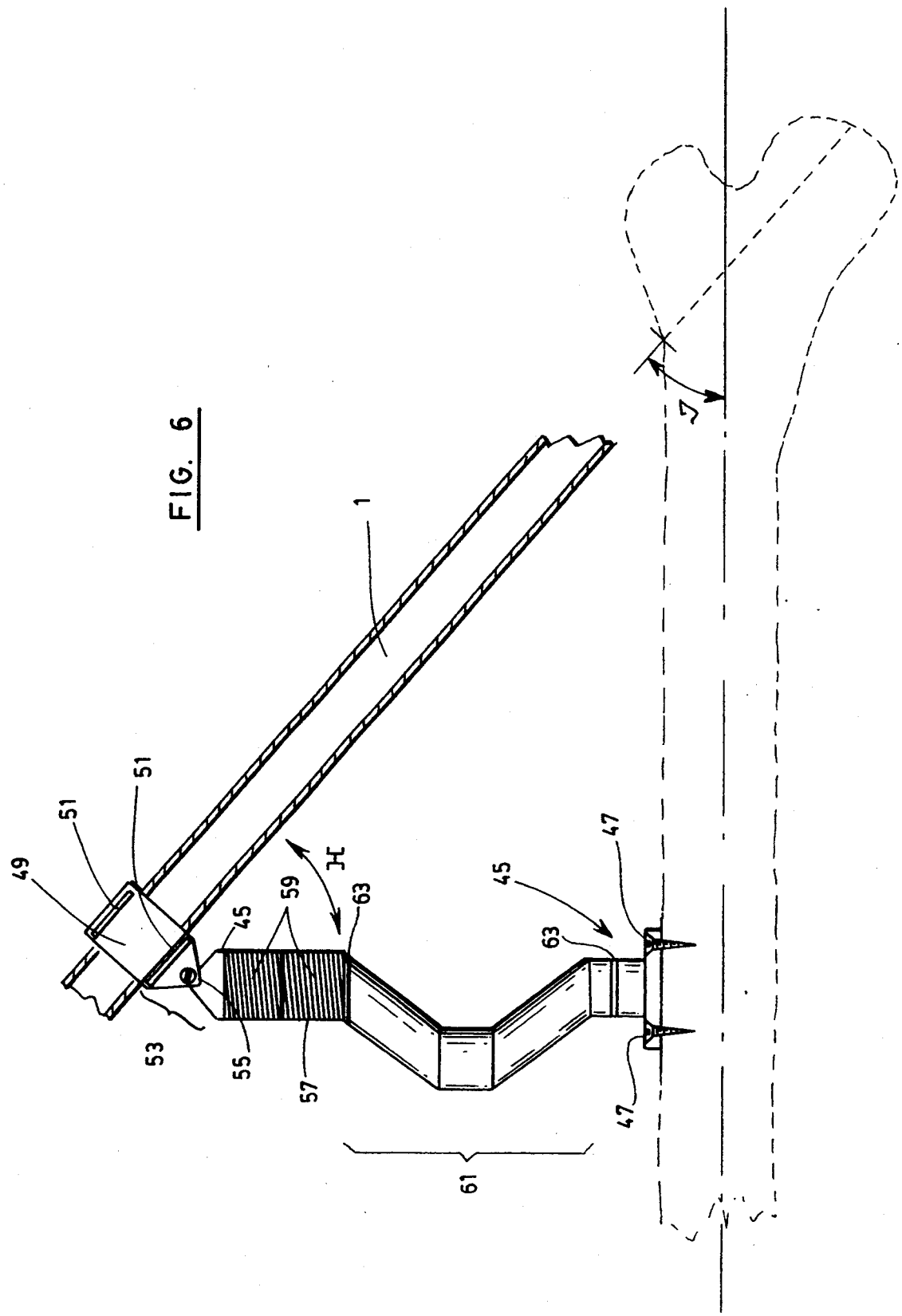

SURGICAL INSTRUMENT FOR CONE-SHAPED SUB-TROCHANTERIC ROTATIONAL OSTEOTOMY

FIELD OF THE INVENTION

The present invention relates to a surgical instrument and to a kit enclosing this instrument, for use to carry out a cone shaped sub-trochanteric rotational osteotomy.

More particularly, the invention relates to a surgical instrument and kit allowing reorientation of the femoral head of a patient according to the specific needs of this patient, so that the sick zone of the femoral head is replaced by a healthy section of the hip's weight bearing zone. The femoral head is then rigidly fixed to the femur, favoring a rapid and efficient rehabilitation for the patient, and reducing the risk of displacement.

BRIEF DESCRIPTION OF THE PRIOR ART

Up to now, certain diseases of the human hip, more precisely the primary or secondary avascular necrosis of the femoral head (caused by cortisone or aloolism, among others) have not been treated satisfactorily or efficiently, especially amongst young adults, when the disease has reached an advanced stage. [See "The Hip and its Disorders", pp. 732–733; see also C.O.R.R., p. 17].

Partial or total prosthetic replacement is a method of treatment available to the patient. Even though this technique has been greatly improved during the last ten years, it cannot, however, be applied to patients younger than fifty, since the duration of the prosthesis is far inferior to the life span of these patients. [See "The Hip and its Disorders", pp. 733–720 ; see also C.O.R.R., pp. 17–18 and; Evarts 2e Ed, p. 2790].

Furthermore, in cases where the disease is still at its early stage, the actual treatment, which consists of a core decompression by removing an 8 to 10 mm of bone from the ill segment of the femoral head, does not guaranty long term termination or control of the disease's progression.

These facts explain why all methods of treatment to date have aimed at slowing the progression of the disease, so that the patient reaches the age where putting in an artificial hip becomes an acceptable choice. [See Rennie & Cruess, p. 1227; see also "The Hip and its Disorders", pp. 710–711 and; C.O.R.R. Nov. 1987, p. 150].

The osteotomy which consist in cutting and realigning the bone is an option that is worth considering when it is feasible. Classical types of osteotomies have the disadvantage of modifying the mechanical axis of the hip and leg and the muscular forces involved. Consequently, this technique calls for a certain compromise which is to the detriment of the hip's biomechanic principles. [See Rennie & Cruess, pp. 1224–1227; see also "The Hip and its Disorders", p. 733 and; Evarts 2e Ed, pp. 1807–1822].

This technique also has certain limitations such as the degree of reorientation possible for the femoral head in the acetabulum. Therefore, when the ill part of the femoral head is not sufficiently distanced from the weight bearing zone of the hip, the result is compromised. [See Evarts 2e Ed, p. 2786; see also C.O.R.R. Nov. 1987, p. 150].

This technique also modifies the proximal morphology of the femur to such a point that placing a future artificial articulation (this being the inevitable fate of the majority of patients suffering from this ailment) can be compromised and risky. The survival of the replacement orthoplasty can thus be affected. [See Evarts 2 e Ed. pp. 2786–2787; see also "The Hip and its Disorders", p. 734].

In fact, there exists only one type of osteotomy, distinct from the so-called classical methods, that does not affect the biomechanics of the hip and that allows for an efficient displacement of the ill part of the weight bearing zone of the femoral head outside of the weight bearing zone of the hip, without modifying the proximal morphology of the femur [See C.O.R.R. Nov. 1987, p. 151], thus without reducing the chances of success in an eventual prosthetic replacement [See Evarts 2e Ed., p. 2788; see also C.O.R.R. Nov. 1987, p. 155]. This technique is the one known as trochanteric osteotomy by femoral neck rotation, as described by Sugioka in 1972 [See Sugioka Y. (1984) Transtrochanteric rotational osteotomy in the treatment of idiopathic and steroid-induced femoral head necrosis, Perthes' disease, slipped capital femoral epiphysis, and ostheoarthrisis of the hip. Clin Orthop. 184, p. 12].

This technique is somewhat less classical, since it is more invasive, and technically malaises so that it can hardly be reproduced by anyone, other than Sugioka himself [See "The hip and its Disorders", p. 733; see also C.O.R.R. Nov. 1987, p. 155]. Other inconvenients are also present in this technique, such as the increasing possibility of avascular necrosis since the vascular supply to the femoral head is terminal. The blood flow coming distally to proximaly: the more proximal the level of the osteotomy being done, the higher the risk of compromising the blood flow to the femoral head, and thus compromising its viability. The great surgical exposure which this technique entails risks directly damaging the blood vessels which go to the femoral head. The detachment of the greater trochanter, the enormous degree of rotation imposed on the femoral head (up to 100 degrees) and the lack of stability of the set-up once the reorientation has been done, are other disadvantages of this technique. [See C.O.R.R. June 1990, p. 197].

SUMMARY OF THE INVENTION

The present invention proposes a surgical instrument and a kit including this instrument, for use to make a cone-shaped cut into the proximal femur of a patient, said cut having a tip located on the postero lateral side of the femur at the sub-trochanteric level, a base located at the trans-trochanteric level and a central axis aligned with the one of the femoral neck.

The aim of the invention is to allow rotational reorientation to various degrees, depending on the need of each patient, of the femoral head in the acetabulum, so as to move the ill zone of the femoral head from the weight bearing zone of the hip towards a non weight bearing zone.

The surgical instrument according to the invention comprises a cutting guide attachable to a centrally hollowed, cervical screw which has previously been inserted into the femoral head along the central axis of the cone to be cut. Once fastened, the guide can freely rotate relative to the cervical screw about the axis of screw.

The instrument also comprises a drilling bit, which passes through the cutting guide into an oblique hole which has a slope corresponding to half the angle of the cone to be cut and which is so placed as to cause the drill bit to penetrate the bone at the level of the lateral wall of the femur as close as possible to the cervical screw. This enables cutting of the cone to be done by lateral displacement of the bit, in a circular motion, which is progressively enlarged as the bit moves in depth. Thus, cutting of the cone is initiated from the tip and completed at the base.

The instrument according to the invention further comprises means to connect the drill bit onto the guide, to drive it in rotation around its own axis, about the axis of the screw; these means being also devised to allow bit to be moved forward which it is driven in rotation.

This invention also includes a surgical kit which includes, in combination:
- a surgical instrument as defined above:
- a chisel which can have up to four cutting wings at one extremity, oriented at 90 degrees from each other and which is devised to be inserted into the cervical screw;
- a compression plate which can be inserted onto the cervical screw after the cone has entirely been cut and the surgical instrument has been removed, this compression plate having a proximal extremity which can contain up to four blades sized to fit into the slits left into the bone by the chisel's cutting wings, said proximal extremity being provided with a central hole sized to fit into the distal extremity of the cervical screw;
- a compression screw insertable on the compression plate and which can be fastened to the cervical screw; and
- a stabilizing hooking member which can be fixed onto the greater trochanter and which can be reattached by compression at the level of the compression plate.

The principal advantages of the surgical instrument and kit, according to the invention when they are used as described hereinafter are the following:
- a substantial reduction in the technical difficulties that may be encountered during the operation, and in the time needed for the operation, so that the loss of blood and morbidity rate associated to the operation are reduced;
- a lesser need for surgical exposure and limb manipulation during surgery;
- a reduction in the risks compromising the viability of the femoral head by proceeding to cut at the sub-trochanteric level rather than at the trans-trochanteric level;
- an efficient osteotomy permitting a degree of reorientation of the femoral head specific to the needs of every patient, without touching the greater trochanter, thus avoiding inconvenients such as non union, pain and other complications which delay the patient's recovery [See Complications of trochanteric osteotomy, C.O.N.A. April 1992, p. 321];
- the conic shape of the cut increases the stability of the set-up as well as the surface of the bone's cut, thereby ensuring a better vascularisation to the proximal metaphyseal fragment;
- the kit and instrument ensure an enhanced stability of the set-up by fixing the compression plate to the femur, so that an early mobilisation and weight bearing are possible; and
- the kit and instrument favor better consolidation of the osteotomy by combining the following factors:

excellent coaptation between the two fragments de part the conic form of the cut and the large contact surface to which it confers; a better vascular supply; and an interfrag-mentary compression. These factors reduce the risk of varus deformation among others, as noted by Sugioka and other authors. [Sugioka Y. (1984) "Transtrochanteric rotational osteotomy in the treatment of idiopathic and steroid-induced femoral head necrosis, Perthes' disease, slipped capital femoral epiphysis, and ostheoarthritis of the hip", Clin. Orthop. 184, p. 12].

The invention and the operational procedure to be followed when it is used, will be better understood upon reading the following non-restrictive description of a preferred embodiment thereof, given with reference to accompanying drawings.

BRIEF DESCRIPTION OF THE DRAWINGS

In the drawings which illustrate the invention:

FIG. 6. is an enlarged schematic side elevational view of the holding arm, of the guide used in accordance with the present invention;

DESCRIPTION OF A PREFERRED EMBODIMENTS OF THE INVENTION

Figure 1:
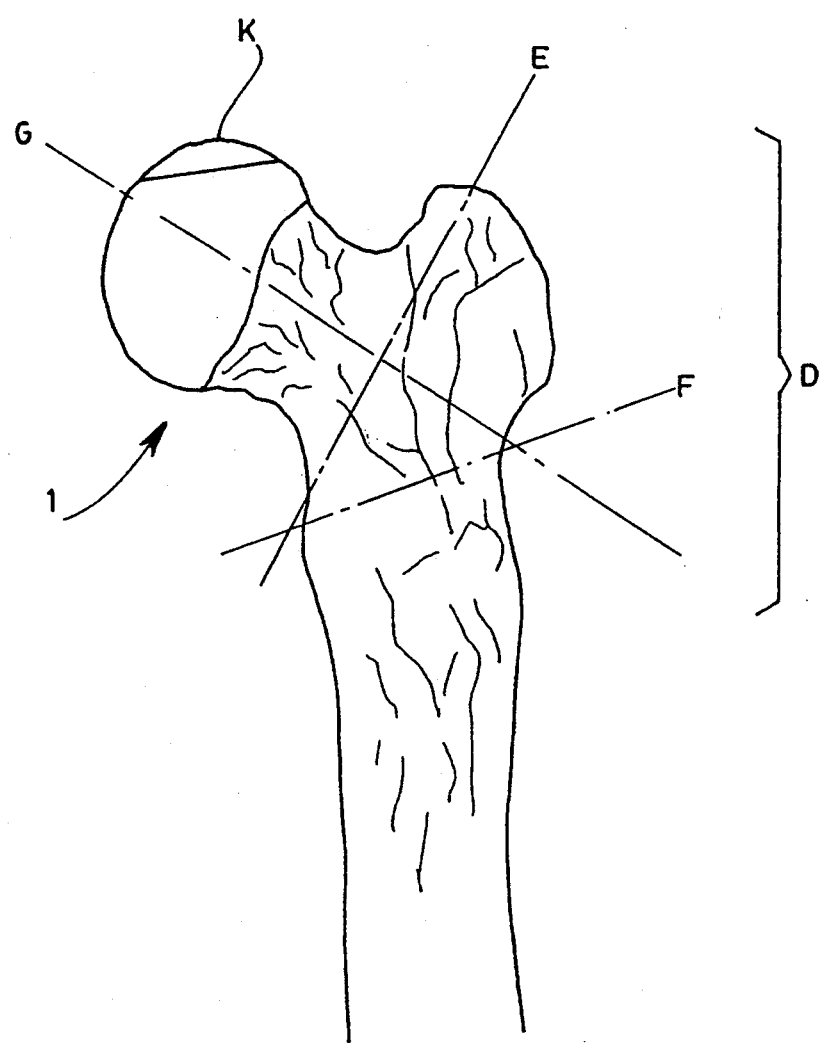
FIG. 1 is a schematic representation of the anterior aspect of the proximal femur.

As aforesaid, the invention relates to a surgical instrument and to a kit for use to carry out a cone-shaped cut into the proximal femur of a patient. FIG. 1 is a schematic representation of the anterior side of a proximal femur D. The tip of the cone to be cut with the surgical instrument according to the invention, is located at the postero-lateral side of the sub-trochanteric level F and the base of the cone is located in the trans trochanteric plane E. The central axis of the cone corresponds to that of the femoral neck G. The purpose of this cut is to reorient the femoral head 1 in the acetabulum, by rotating it to various degrees according to the needs of each patient, so as to move the ill zone K of the femoral head 1 from the weight bearing zone of the hip towards a non weight bearing zone.

Figure 2:
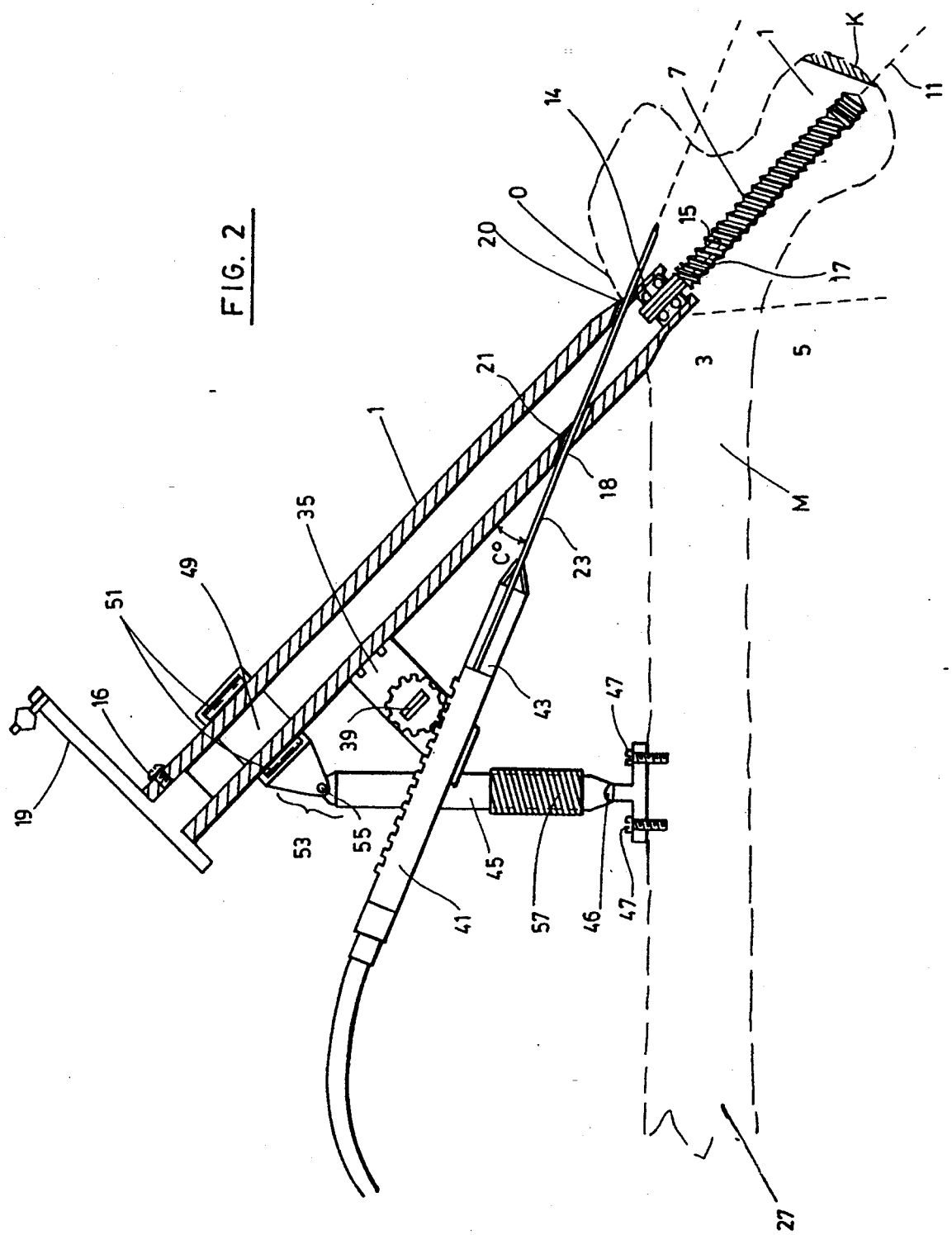
FIG. 2 is a schematic side elevational view of a surgical instrument according to the invention, shown partly in cross-section, when positioned onto a patients femur.

FIG. 2 is a schematic side elevational view of the surgical instrument according to the invention, shown mounted on a patient's femur. The surgical instrument includes a cutting guide 1 made from an easily sterilizable material such as stainless steel. This guide has a proximal extremity 3 provided with means 5 for use to connect in a rigid yet stable manner the guide 1 to a centrally hollowed cervical screw 7 which has previously been driven in the femur M, more precisely along the central axis 11 of the cone 13 to be cut.

Figure 3:
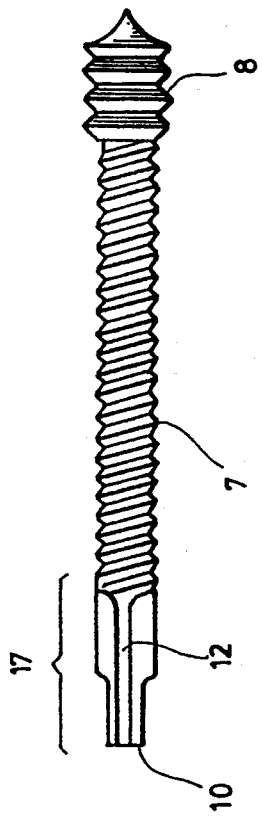
FIG. 3 is a schematic side elevational view of the centrally hollow, cervical screw forming part of the instrument according to the invention.
Figure 8A:
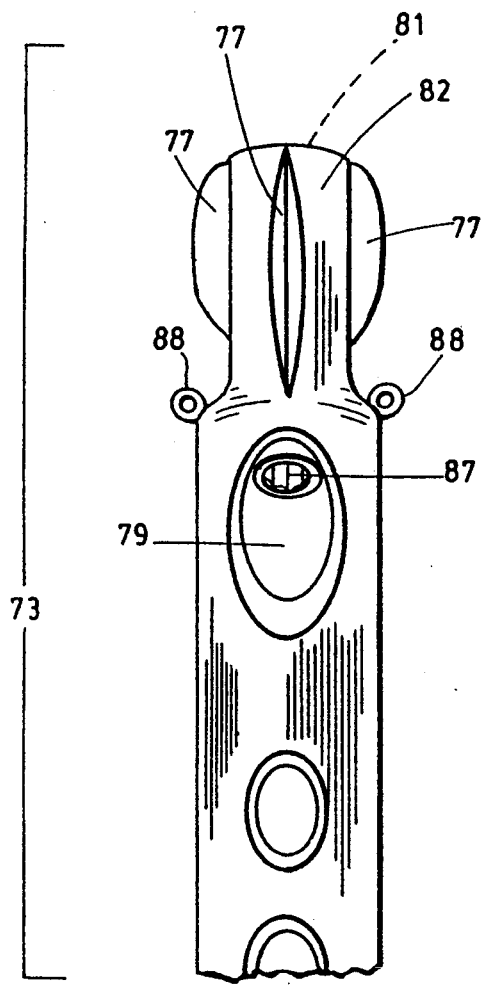
FIG. 8A is an enlarged schematic view of the compression plate and of the compression screw of the kit according to the invention.

FIG. 3 is an enlarged schematic view of the cervical screw 7. This screw 7 has a sharp proximal end 8 that is threaded to facilitate its penetration in the bone during its insertion and to help it in remaining in place. This screw also has a distal end which has an external section 10 which, as shown in FIG. 8a, in sized to fit perfectly in the proximal end 82 of the barrel-receiving hole of the compression plate 73, and an internal section 12 which is hollowed and threaded to allow connection of the cutting guide 1 (FIG.2) and subsequently of the compression plate 73 with the help of a compression screw 87 (see FIG. 8A). This centrally hollowed, threaded cervical screw 7 must be made of solid, resistant and easy sterilizable material which does not generate an undesirable immune reaction in the patient, since this screw can remain in the patient's bone for many months and even years, in some cases.

As illustrated in FIG. 2, the cervical screw 7 is of such a dimension as to provide a strong grip to the cutting guide 1 and to the other means used thereafter which depend on said screw 7 for being held in place, without significant damages to the bone M.

According to the invention, the means 5 used to connect the cutting guide 1 to the screw 7 must give total liberty of rotation to the guide relative to the screw about the axis 11 of said cervical screw.

The connecting means 5 can include a screw 15 sized to fit into the interior section 12 (FIG. 3) of the centrally hollowed and threaded screw 7, the other portion of the screw ending inside the cutting guide 1, where it prevents the cutting guide to move laterally or along the axis 11 of the cervical screw 7, while giving it total liberty of rotation around the axis 11, with, for example, the help of a ball bearing 14.

A detachable handle 19 can be fastened with the help of a screw 16 to the distal end of the guide 1, to turn the guide manually around itself about the axis 11 of the threaded screw 7. When detached, the guide 1 and the handle, are easy to sterilize.

The cutting guide 1 has an oblique hole 21, whose entrance 18 can be located somewhere half way between the distal end of the guide 1 and its proximal end 3. The exit 20 of the hole 21 is located at the level of the proximal end 3. The diameter of this hole 21 corresponds approximately to that of the drill bit 23. The angle c of the hole 21 with respect to the axis 11 of the cervical screw 7 can vary between 25 and 35 degrees, so that the drill bit 23 which passes through the cutting guide 1 of this hole 21 is equal to the angle A of the cut 13 to be made. The guide 1 is placed in such a way that it permits the drill bit 23 to penetrate the bone at the level of the lateral wall of the femur M, as close as possible of the threaded screw 7, so as to initiate cutting of the bone at the tip of cone 13.

Figure 4:
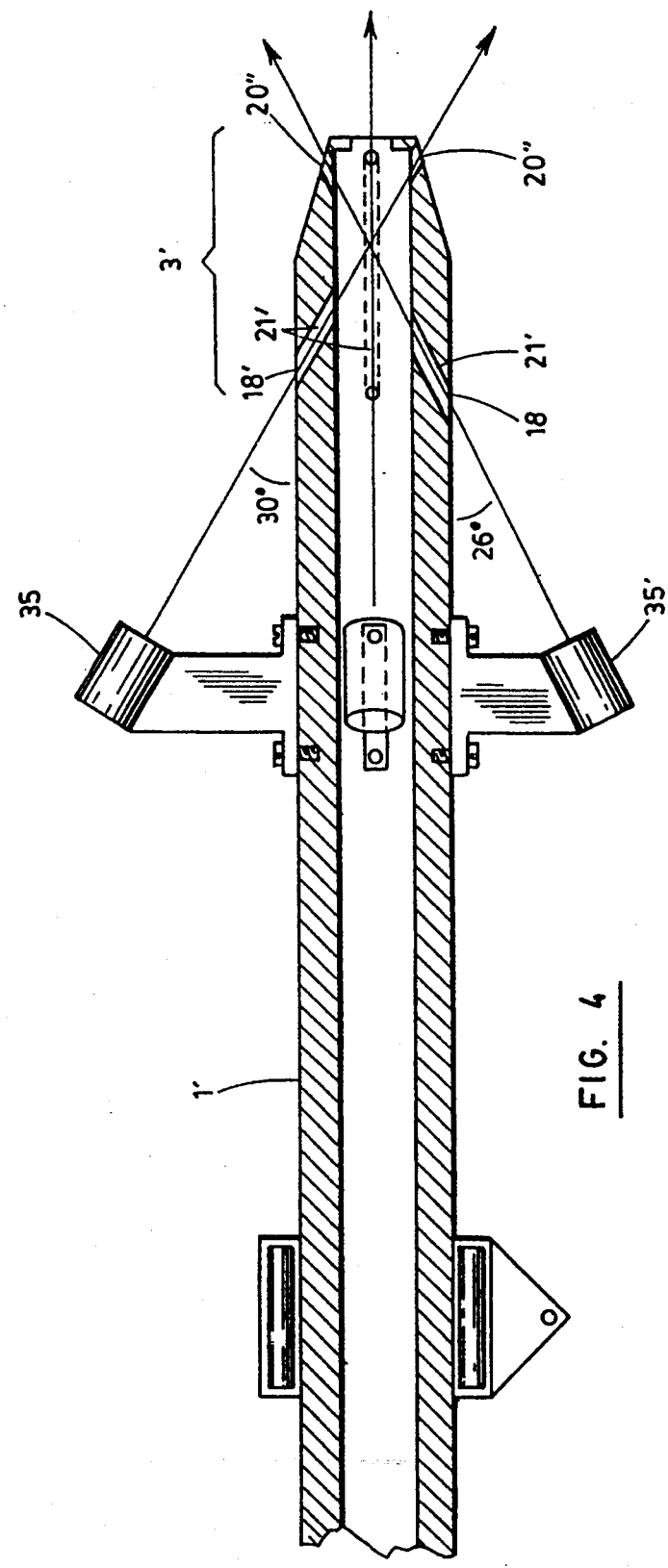
FIG. 4 is an enlarged schematic view of a variant for the cutting guide forming part of the instrument.

FIG. 4 is an enlarged schematic view in cross-section of a variant of the cutting guide according to the invention. The cutting guide 1' shown in FIG. 4 has many oblique holes 21'. The angles these holes 21' are different and range between 25 and 35 degrees, so that the drill bit 23 (FIG.2) which passes through the cutting guide 1' through one of these holes 21', can extend at an angle which corresponds to the desired angle A of the cut (FIG 2). This makes the same cutting guide 21' useful with most of the patients whatever be the dimension and conformation of their proximal femurs.

As illustrated in FIG. 2, cutting of cone 13 is done with the help of a drilling bit 23. The bit 23 which is driven in rotation about its own axis is moved forward in the bone while the cutting guide is turned with the help of the handle 19, so as to initiate the cut at the tip of the cone 13 on the postero lateral side at the sub-trochanteric level F (see FIG. 1), and to end the cut at the base of this cone, i.e. at the trans-trochanteric level E. (see FIG. 1)

Figure 5:
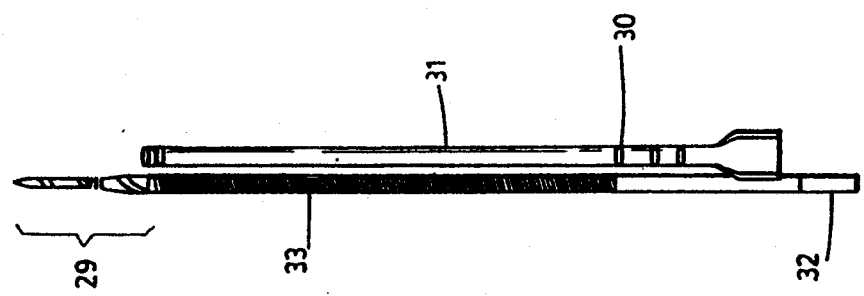
FIG. 5 is an enlarged schematic view of the drill bit and of its protection guard, for use in the instrument according to the invention.

FIG. 5 is a schematic representation of the drill bit 23. During cutting of the bone M (FIG. 2), the drill bit 23 is subjected to very important lateral pressure and therefore must be made of an alloy giving it solidity and resistance, while allowing it to remain relatively flexible. The particular conformation of the cutting end portion 29 of the bit 23, which has a very sharp cutting thread on its periphery and on its pointed end, allows it to easily penetrate the bone M (as illustrated in FIG. 2) and to cut it laterally. To ensure greater protection of the bit 23, its smooth, non cutting end portion and its middle portion can advantageously be surrounded by a slim and resistant protection guard 31 made of a rigid alloy. This protection guard 31 stops short of the end portion 29 of bit 23 and of the non-cutting portion of the bit which allows it to be connected to the cutting guide 1 (FIG. 2) and be rotated. The protection guard 31 can also contain one or more ball bearings 30, placed at its extremities or elsewhere, as to reduce the friction of the bit against while the bit 23 is rotating. In a possible variant of the drill bit 23, a flexible cable or spring 33 can constitute the middle portion of the bit, excluding the cutting end portion 29 and the non-cutting portion 32 of the bit, so that the spring or cable absorbs the lateral stresses to which the bit 23 is subjected during cutting. In -this variant where middle portion of the bit is a flexible spring or cable 33, the rigid protection guard 33 is necessary to make it useful.

The drill bit 23 must be long enough to extend over the distance between the means used to support it, to push it forward and to drive it in rotation, and the base of the cone, at the trans-trochanteric level E (see FIG. 1).

As illustrated in FIG. 2, means are provided to connect the drill bit and drive it in rotation. These means include a supporting arm 35, which can or cannot be permanently fastened to the cutting guide, and is oriented and positioned so that the angle of orientation of the drill bit 23 corresponds to that of angle C and the opposite angle A required for the cut of cone 13. The cutting guide 1' illustrated in FIG. 4 must of course include several supporting arms 35', on per hole 21' made into the cutting guide 1'. The supporting arms 35' are made out of solid materials which can be easily sterilized.

As illustrated in FIG. 2, the means by which the drill bit 23 is connected whether or not said means consists of said supporting arms 35, advantageously includes a rectilinear sliding system 38 which allows the drill bit 23 to be moved forward along its axis. The sliding system 38 may include an adjustment screw with a great number of threads per unit of length 39, which makes the bit advancable in a very precise manner such being of value in a delicate operation such as a conical osteotomy.

The means used to drive the drill bit 23 in rotation may consist of a turbine 41 attached to the supporting arm 35 or not, and oriented at the same angle, angle A' that the one chosen for the cut of cone 13. This turbine 41 can be activated either by air or gas or with the help of an electric motor or other means. It has in its proximal extremity 43, means to attach the drill bit 23, so that it can drive the same in rotation. These means must be made of solid and resistant material which can be easily sterilized, such as stainless steel.

The turbine 41 is preferably adjustable to rotate the drill bit 23 at different speeds, depending on specific needs. The turbine 41 can be moved forward by the rectilinear sliding system 38 or can be an integral part of it if there is one. Alternatively it can be moved forward by other means, provided that it extends at the same angle as the angle, in the angle of cut A of the cone 13 and allowing the drill bit 23 to be moved forward and driven in rotation at the same time.

The cutting guide can held by a holding arm 45 which is itself attachable to the femur M with the help of a screw 47, for example. FIG. 6 is an enlarged side elevational schematic view of this supporting arm 45. The attachment means 49 used to attach the guide 1 to the supporting arm 45 are devised in such a manner as to allow the guide to be rotated about the axis of the threaded screw 11. The attachment means 49 may include an efficient ball bearing system 51. These means 49 may also include means to allow variation of the angle H between the holding arm 45 and the guide 1, (see FIG. 6) so as to accommodate for variations encountered in patients in the dimension and conformation of their proximal femur. These means can include a flexible joint 53 which links the supporting arm 45 and the attachment means 49. This joint 53 can be strongly immobilized with, for example, a locking screw 55. Another joint 46 can also be provided at the base of the supporting arm 45, fixed to the cone M.

This supporting arm 45 is preferably adjustable in length so as to compensate for any variation in the angle J between the bone M and the guide 1. Such an adjustment can be achieved with a threaded cylinder 57 filed onto the ends of two opposing screws 59, that respectively extend superior and inferior parts of the holding arm. The threaded cylinder 57 has threads on its interior surface, so that when it is turned on either side,the length of the holding arm 45 increases or is reduced. The holding arm 45 can also have a central section 61 which is in the shape of a curve, this section having means to rotate on itself completely to allow the guide 1 to rotate 360 degrees and thus to complete cutting of the cone 13 (FIG.2). These means may include a bearings 63 located at each end of the curved section 61.

The surgical kit according to the invention includes the surgical instrument whose structure has been described above, as well as other components described hereinafter, which include a chisel 65, a compression plate 73, a compression screw 87 and a stabilizing hook 93.

Figure 7B:
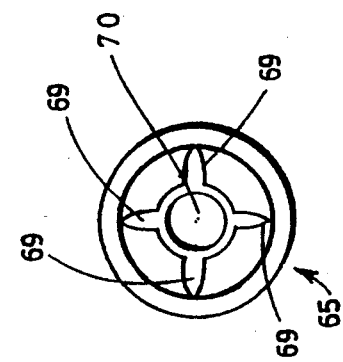
FIG. 7B is a schematic top plan view of the chisel shown in FIG. 7A.
Figure 7A:
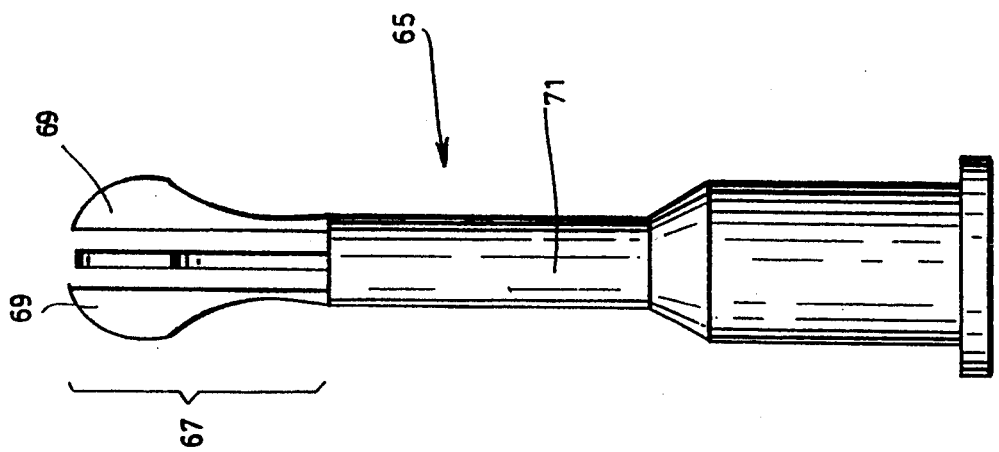
FIG. 7A is an enlarged schematic side elevational view of the chisel used in the kit according to the invention.

FIG. 7a is an enlarged schematic side elevational view of the chisel 65. This chisel 65 has an inner cavity 70 (FIG. 7B), which is intended to receive the distal end 17 of the cervical screw 7 (see FIG. 3), before the cutting of the bone. This chisel 65 has up to four cutting wings 69 projecting from its distal end 67, the wings being sharpened on their external side. As illustrated in FIG. 7B which is a top plan view from the distal end of the chisel the cutting wings 69 are oriented at 90 degrees from each other. When the chisel 65 is inserted on the cervical screw 7 (FIG. 2), the wings 69 are positioned to cut the bone at an angle relative to the axis of the femur 27, which corresponds to the angle of rotation B (see FIG. 10A) at which the femoral head must be rotated. Of course, the chisel 65 could have a greater or smaller number of wings 69, provided that these wings are adjusted at an equal distance from each other. Once the chisel has been inserted in the cervical screw 7 (FIG.3) and has cut the bone, the chisel 65 is removed. The chisel 65 can be made from a resistant and solid substance which can be easily sterilized.

FIG. 8A is an enlarged schematic view of the compression plate 73 and of the compression screw 87 used in connection with the plate 73. The plate 73 has a fondle and a proximal extremity 82 that extends at angle, and is shaped as a barrel, with a central hole 81 sized to fit onto the external section 10 of the cervical screw 7. The barrel 82 of tile compression plate 73 is externally provided four blades 77 sized to fit into the slits left into the bone by the cutting wings 69 of the chisel 65. Once the bone has been cut and the surgical instrument removed (FIG. 2), the compression plate 73 is inserted onto.

Figure 10B:
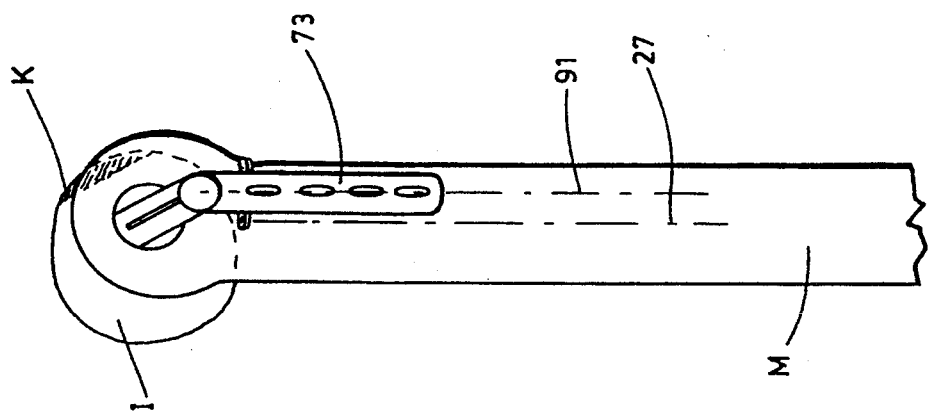
FIG. 10B is a schematic view similar to that of FIG. 10A, slowing the relation between the compression plate and the femoral axis, after rotation of the femoral head.
Figure 10A:
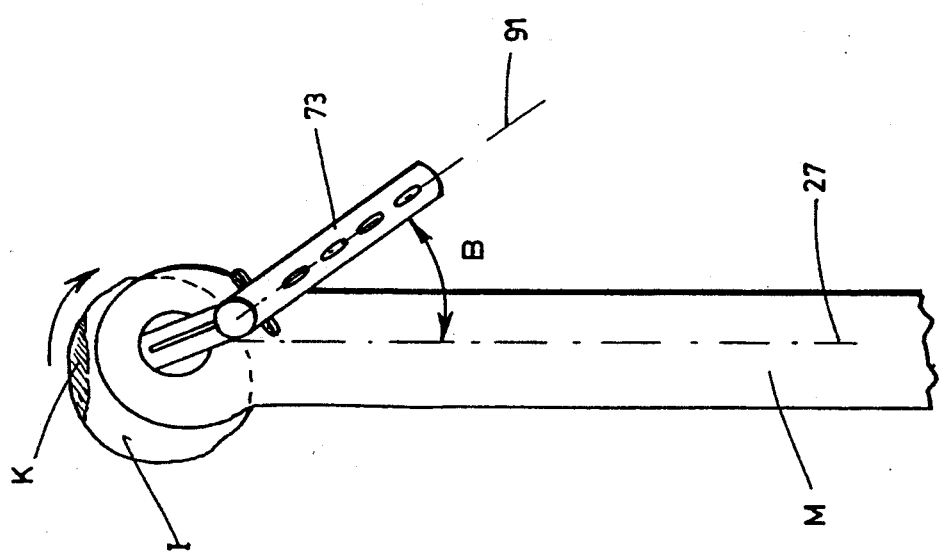
FIG. 10A is a schematic view slowing the relation between the compression plate and the femoral axis, before rotation of the femoral head.

FIG. 10A shows the relative position of the compression plate 73 with respect to the femoral axis 27. Before rotation of the femoral head I, the axis 91 of the handle of the compression plate 73 forms an angle with the axis 27 of the femur M, which corresponds to the angle B by which the femoral head I must be rotated so that the ill zone K be sufficiently distanced from the weight bearing zone of the hip. FIG. 10B shows the relative position of the compression plate 73 with respect the femural axis 27. As can be seen, after rotation of the femoral head I, the compression plate 73 is aligned with the axis 27 of the femur M, where it may then be fastened.

Figure 8B:
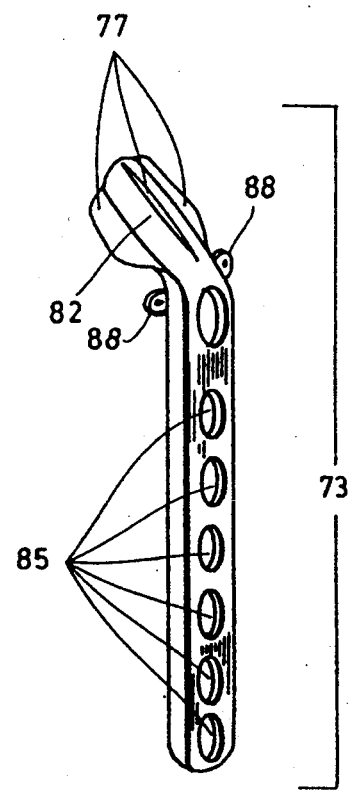
FIG. 8B is an enlarged lateral schematic view of the compression plate shown in FIG. 7A.

As shown in FIG. 8A, tile compression plate 73 has a open cavity 81 in its barrel 75. The axis of this cavity is oriented in such a way that it corresponds to the axis 11 of the cervical screw 7. As shown in FIG. 8B which is an enlarged schematic view of the compression plate illustrated in FIG. 8A, the barrel 82 of the compression plate 73 extends at angle corresponding to the neck-diaphysial angle, so that the distal part or handle of the compression plate 73 can rest directly on the patient's femur M. The handle of the compression plate 73 has a given number of holes 85 which allow the compression plate to be fastened to the femur M (FIG. 2), with, for example, the help of one or more screws. The compression plate can also have eyelets 88 which allow stabilizing hooks to be fastened as will be explained hereinafter. The compression plate 73 is made of a solid and resistant substance which is hypoallergenic and which can be easily sterilised since it can remain in the patient for many months or even years in some cases.

As illustrated by FIG. 8A, the compression screw 87, which is made of a solid and resistant substance that can be easily sterilized and is hypoallergenic, is intended to be inserted in the compression plate 73, in the cervity 81 of the barrel 82 so as to rest in the inner part 12 of the cervical screw 7 (FIG. 3). This allows connection of the compression plate 73 to the cervical screw 7 so that the femoral head I in its new position, is solidly fastened to the femur M (FIG. 10B).

Figure 9:
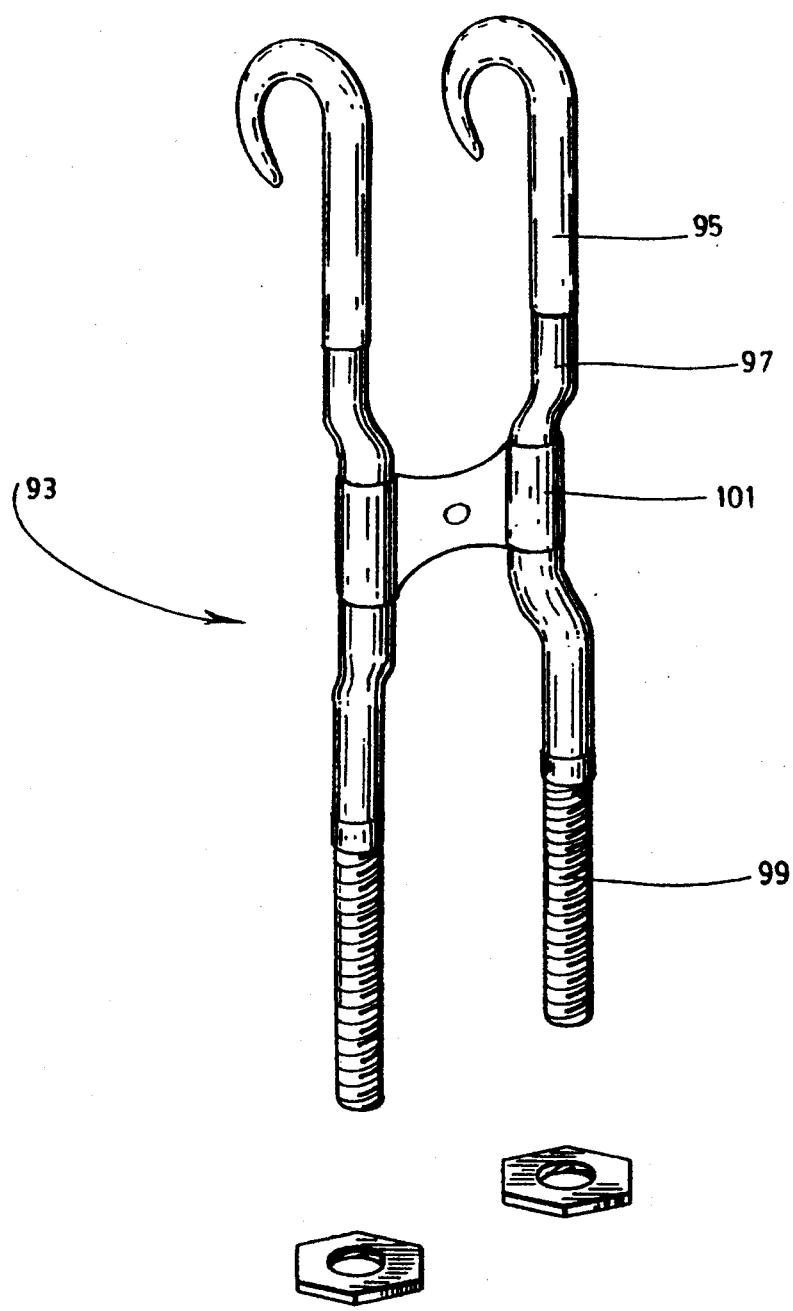
FIG. 9 in an enlarged schematic view of the stabilizing hook member, used in accordance with the present invention.

FIG. 9 is an enlarged schematic view of the stabilizing hook 93 member used in the kit according to the invention. The stabilizing hook 93 member includes two hooks 95 are intended to be fastened to the tip 0 of the greater trochanter (see FIG. 2). Two flexible metallic cables 97 extend from these hooks 95. The stabilizing hook member 93 also includes a cable coupling plate 101 which tightens up the middle part of the metallic cables 97, so as to permit a better distribution of the forces on the curve of the trochanter mass. The cable coupling plate 101 which can be moved on metallic cables 97 and can be fastened there along in any desired location. The plate 101 can also have an opening in its center, in which a screw can be inserted perpendicularly to the ostheotomic line, so as to increase the compression of the bony fragments at that level. At their distal extremities, the metallic cables 97 are extended by two threaded screws 99 which allow solid fastening of the stabilizing hook member 93 to eyelets 88 provided for this purpose in the compression plate 73 (see FIG. 8A), with the help of bolts or other means. Fastening of the metopic cables 97 increases the compression between the bony fragments (between the greater trochantery 0 (FIG. 1) and the cone 13), thereby allowing for an increased protection of the greater trochanter O (FIG. 1) whose chances for fractures are increased by the cut during the patient's premature mobilisation. The stabilizing hook member 93 is of course made of a solid and resistant substance which is hypoallergenic and can be easily sterilized.

The invention will be better understood upon reading of the following description of the operational procedure that must be followed when using the surgical instrument and the surgical kit according the invention. This description will refer to the accompanying drawings and more particularly to FIG. 2.

Step 1

Before the surgery, an X-ray study obtained in the AP plan in neutral and internal rotation and in the lateral plan, allows to precisely determine:
a) the angle A between the side of the cone and the axis of the femoral neck 11. This, when respected should allow the cut to come out in the trans-trochanteric plane E (FIG. 1). This plan E (FIG. 1) corresponds to the base of the cone; and
b) the angle B as shown in FIG. 10A, which side a schematic view of the position of the compression plate 73 with respect to the femur's axis 27 before rotation of the femoral head I, which angle B corresponds to the rotation to be made at the level of the femoral head I as to remove the ill zone K from the hip's weight bearing zone.

Step 2

The patient, laying down on his non-operative side, is placed on an orthopaedic traction table, so that the portion of his or her body to be operated is completely extended and is stabilized distally at the foot. During the pre-operative fluoroscopy and during the entire operation, the side of the hip which is not being operated and, on which the patient is lying, is flexed to avoid a superimposition of the images of the opposite femur M with the one of the hip to be operated.

Step 3

Following a lateral approach of the hip and with the help of fluoroscopy control, a guiding pin is installed into place. The pin must be perfectly centred on the axis 11 of the femoral neck in the antero posterior and lateral planes. The axis of this guiding pin must correspond to the central axis 11 of the cone to be cut 13.

Step 4

A hole centred on the guiding pin is made with a drill and a cannulated bit. This operation allows subsequent insertion of the centrally hollowed, cervical screw 7 in the pin's axis. The length of the screw 7 must be of such a dimension as to correspond to the space separating the articulation and the lateral wall of the femur (area of the bit's entrance), which is less than 2 cm but sufficient to give, once it is inserted in the bone, 1 cm of freedom to both its extremities while making it sure that 1 cm is free and the articulatory level is not tapped immediately. The chisel 65 (FIG. 7A, 7B) is then introduced into the cervical screw 7 so as to extend along the axis 11 of this cervical screw 7. As aforesaid, the wings 69 (FIG. 7A) of the chisel 65 (FIG. 7A) are placed at a 90 degree angle from each other (FIG. 7B). During the insertion of the chisel 65 (FIG. 7A) onto the cervical screw 7 (FIG. 2), the cutting wings are oriented in reference to the femoral axis 27 (FIG. 10A) so they slit the bone at an angle corresponding to the angle of rotation B (FIG. 10A), previously calculated from the results obtained during step 1. This angle B (FIG. 10A) corresponds to the degree of rotation which the femoral head I must undergo to remove the sick zone K from the hip's weight bearing zone. Insertion of the chisel 65 (FIG. 7A) facilitates subsequent installation of the compression plate 73 (FIG. 8A) whose blades 77 (FIG. 8A) fit perfectly into the slits made into the bone by the cutting wings 69 (FIG. 7A) of the chisel 65 (FIG. 7A).

Step 5

The chisel is then removed and the cutting guide 1 is fastened onto the centrally hollowed, cervical screw 7 with the help of a small screw 15. The position of the guide relative to the bone M must be adjusted in such a way that the exiting point 20 of the hole 21 made in the guide 1 allows the drill bit 23 entry in the bone M as close as possible to the tip of the cone 13. The angle of entry 21 of the drill bit must correspond to the angle A. The fixation of the guide 1 in the cervical screw 7 allows the guide 1 to freely rotate about the axis 11 of this screw 7.

Step 6

The holding arm 45 is fastened to the distal part of the guide 1 as well as to the femur M, with the help of a screw 47. This holding arm 45 eliminates the bending torque which would other wise take place at the junction of the guide 1 with the screw 7 during cutting of the bone. This holding arm 45 is adjustable in length, as well as in angle D relative to the cutting guide 1, so as to accommodate for variation of the angle F (FIG. 6) between the femoral axis 27 (AP) and the axis 11 with which the guide 1 is aligned. These variations depend on the dimension and conformation of the proximal femur of the patient. Fastening 49 of the holding arm 45 to the guide 1 allows the guide to freely rotate about the axis 11 of the cervical screw 7.

Step 7

The turbine 41 is then assembled on the guide 1 via the supporting arm 35 whose slant corresponds to the angle of cut A, previously measured. A rectilinear sliding system 38 allows, under manual control with the help of a adjustment screw to move the turbine 41 forward in the axis along which it is assembled.

Step 8

The drilling bit 23 is then fastened to the turbine 41. This bit 23 extends through the cutting guide 1 in the hole 21 whose angle C (FIG. 4) corresponds to the angle of cut A determined during step 1. The drill bit 23 must penetrate the bone M at the lateral wall of the femur as closely as possible to the cervical screw 7. The cut of bone M is done by lateral displacement of the drill bit 23 in a circular motion which the bit is progressively moved forward. This is made possible by turning the guide 1 manually with the help of the handle 19. Successive "pushes" of 1 or 2 mm are added to these movements of the drill bit 23 via the adjustment screw 39 which activates the rectilinear sliding system 38. These two movements, rectilignal and circular, which can be done manually and alternatively, allow for progression of the drill bit in the bone M, by making it follow the tracks of a round helix with a diameter which becomes increasingly bigger, thereby forming the required cone 13. Cutting of the cone 13 finishes at the base, in the trans-trochanterian plane.

Step 9

Once the cone is cut and the proximal fragment is freed, the surgical instrument is removed. At this stage, the cervical screw may become too protuberant at the femur's lateral wall. As a result, it may become impossible to compress the bone. This may be drive to a loss of bone thickness corresponding to the diameter of the drill bit 23 and of its guard 31 (FIG. 5) during the cut. Thus, if necessary, the centrally threaded cannulated screw 7 can be pushed in closer to the articulation while leaving a minimum of 0.5 cm between the proximal extremity of the cervical screw 7 and the articulation.

The compression plate 73 and its blades 77 (FIG. A) are then introduced on to the centrally threaded cannulated screw 7 (FIG. 2) according to the same orientation (angle B, FIG. 10A) of the slits left in the bone by the cutting wings 69 of the chisel 65 (FIG. 7A). The angle formed between the axis 91 of the compression plate 73 and the femur's axis 27, must correspond to angle B, which is the angle of rotation to be met by the femoral head I (FIG. 10A). The compression plate (FIG. 7A) is solid held to the femoral head I (FIG. 10A) by means of its hallow barrel (FIG. 8A) which fits into part 10 of the distal extremity 17 of the cervical screw (FIG. 3) and by means of its four blades 77 (FIG. 8A). Then, the plate serves as a handle to manipulate the cone 13 freed from all ties. Rotation is then given to the cone (FIG. 10A) to obtain the new position needed relative to the acetabulum, thus moving the ill zone K to a non weight bearing site and at the same time, allowing the compression plate 73 (FIG. 10B) to sit on the femur's axis.

Once the compression plate 73 and the femur's axis 27 are perfectly aligned, the compression plate 73 is then fastened on the femur M (FIG. 10 B) with screws.

Step 10

The compression screw 87 is now inserted into the compression plate's 73 cavity 80 (FIG. 8A) so that it reaches the inside of the cervical screw 7 to which it is fastened. This operation ends the fastening of the two bone fragments. The new position between normal cartilages, on the femoral head I with the acetabulum, is thus achieved, and accordingly, joint congruence is found once again.

Step 11

The stabilizing hook member 93, as illustrated in FIG. 10, is fastened at the tip of the greater trochanter O with the help of its rigid hooks 95 (FIG. 9). The flexible metallic cables 97 extend from these hooks. The stabilizing hook member also has a cable coupling plate 101 which tightens up the middle part of the metallic cables 97 (FIG. 9), to allow a better distribution of the forces over the curve of tile trochanter mass. At their distal extremities, these metallic cables 97 are extruded by two threaded screws 99, which permit solid fastening of the stabilizing hook member 93 (FIG. 9) to the eyelets 88 of the compression plate 73. (FIG. 8A), with the help of bolts. They also permits to tension the metallic cables 97 and increase the compression between the bony fragments (i.e between the greater trochanter O and the cone 13, thereby allowing an increased protection of the greater trochanter O (FIG. 1) from fracturing in the case of premature mobilisation of the patient.

I claim:

1. A surgical instrument for use to make a cut shaped as a cone in the proximal femur of a patient, said cone having a tip located on the postero lateral side at the sub-trochanteric level, a base located at the trans-trochanteric level and a central axis aligned with the axis of the femoral neck, all in the aim of reorienting at a given degree the femoral head in the acetabulum in a rotational fashion depending on the need of the patient, so as to transfer an ill zone in said femoral head from a weight bearing zone to a non-weight bearing zone, said instrument comprising:

a) a cutting guide attachable to a hollowed cervical screw previously inserted into the femoral head along the central axis of the cone to be cut, said guide, once fastened, being free to rotate relative to said cervical screw around the axis of said cervical screw;

b) a drilling bit passing through said guide in an oblique hole having a slope which corresponds to half the angle of the cone to be cut, in order to penetrate the bone at the level of the lateral wall of the femur as close as possible to said cervical screw and thus cut the cone by lateral displacement of the bit in a circular motion which is progressively enlarged as the drill bit moves forward in the femur head, thus initiating cutting of the cone from its tip to its base; and c) means to connect the drill bit on the guide to drive it in rotation about its own axis, said means being also devised to allow the bit to be moved forward while it is rotated about the axis of the cervical screw, wherein said means to connect said drill bit and drive it in rotation includes a rectilinear sliding system comprising an adjustment screw with a large number of threads per unit of length, for advancing said bit along its own axis.

2. An instrument as defined in claim 1, wherein said means to connect said drill bit and drive it in rotation also includes a supporting arm attachable to said guide to keep said bit in alignment with said oblique hole.

3. An instrument as defined in claim 2, wherein means to connect said drill bit and drive it in rotation also includes a turbine.

4. An instrument as defined in claim 3, wherein said guide includes at least four of said oblique holes each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

5. An instrument as defined in claim 2, wherein said guide includes at least four of said oblique hole each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

6. An instrument as defined in claim 1, wherein said guide has a detachable handle which allows said guide to be turned around itself about the axis of said cervical screw.

7. An instrument as defined in claim 1, wherein means to connect said drill bit and drive it in rotation also includes a turbine.

8. An instrument as defined in claim 7, wherein said guide includes at least four of said oblique hole each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

9. An instrument as defined in claim 1, wherein said guide includes at least four of said oblique hole each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

10. A surgical instrument for use to make a cut shaped as a cone in the proximal femur of a patient, said cone having a tip located on the postero lateral side at the sub-trochanteric level, a base located at the trans-trochanteric level and a central axis aligned with the axis of the femoral neck, all in the aim of reorienting at a given degree the femoral head in the acetabulum in a rotational fashion depending on the need of the patient, so as to transfer an ill zone in said femoral head from a weight bearing zone to a non-weight bearing zone, said instrument comprising:

a) a cutting guide attachable to a hollowed cervical screw previously inserted into the femoral head along the central axis of the cone to be cut, said guide, once fastened, being free to rotate relative to said cervical screw around the axis of said cervical screw;

b) a drilling bit passing through said guide in an oblique hole having a slope which corresponds to half the angle of the cone to be cut, in order to penetrate the bone at the level of the lateral wall of the femur as close as possible to said cervical screw and thus cut the cone by lateral displacement of the bit in a circular motion which is progressively enlarged as the drill bit moves forward in the femur head, thus initiating cutting of the cone from its tip to its base; and c) means to connect the drill bit on the guide to drive it in rotation about its own axis, said means being also devised to allow the bit to be moved forward while it is rotated about the axis of the cervical screw, wherein said guide is supported by a holding arm which is attachable to the femur in such a manner as to allow said guide to rotate about the axis of said cervical screw.

11. An instrument as defined in claim 10, wherein said holding arm includes means to adjust the angle of attachment of said holding arm to said guide and the angle of attachment of said holding arm to the femur, and means to adjust the length of the said holding arm.

12. An instrument as defined in claim 11, wherein said holding arm has a curve shaped central section, said central section having means allowing it to rotate completely about itself.

13. An instrument as defined in claim 10, wherein said holding arm has a curve shaped central section, said central section having means allowing it to rotate completely about itself.

14. An instrument as defined in claim 10, wherein means to connect said drill bit and drive it in rotation includes a rectilinear sliding system comprising an adjustment screw with a large number of threads per unit of length, for advancing a said bit along its own axes.

15. An instrument as defined in claim 14, wherein means to connect said drill bit and drive it in rotation also includes a turbine.

16. An instrument as defined in claim 15, wherein said guide includes at least four of said oblique hole each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

17. An instrument as defined in claim 10, wherein said guide includes at least four of said oblique hole each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

18. A surgical instrument for use to make a cut shaped as a cone in the proximal femur of a patient, said cone having a tip located on the postero lateral side at the sub-trochanteric level, a base located at the trans-trochanteric level and a central axis aligned with the axis of the femoral neck, all in the aim of reorienting at a given degree the femoral head in the acetabulum in a rotational fashion depending on the need of the patient, so as to transfer an ill zone in said femoral head from a weight bearing zone to a non-weight bearing zone, said instrument comprising;.

a) a cutting guide attachable to a hollowed cervical screw previously inserted into the femoral head along the central axis of the cone to be cut, said guide, once fastened, being free to rotate relative to said cervical screw around the axis of said cervical screw;

b) a drilling bit passing through said guide in an oblique hole having a slope which corresponds to half the angle of the cone to be cut, in order to penetrate the bone at the level of the lateral wall of the femur as close as possible to said cervical screw and thus cut the cone by lateral displacement of the bit in a circular motion which is progressively enlarged as the drill bit moves forward in the femur head, thus initiating cutting of the cone from its tip to its base; and c) means to connect the drill bit on the guide to drive it in rotation about its own axis, said means being also devised to allow the bit to be moved forward while it is rotated about the axis of the cervical screw, wherein said means to connect said drill bit and drive it in rotation includes a turbine.

19. An instrument as defined in claim 18, wherein said guide includes at least four of said oblique holes each with a different slope, said slopes ranging between 25° and 35°, and wherein said means to connect said drill bit and drive it in rotation are so devised as to allow said drill bit to pass into any one of said four oblique holes to as to extend at the angle of the corresponding slope.

20. A surgical instrument for use to make a cut shaped as a cone in the proximal femur of a patient, said cone having a tip located on the postero lateral side at the sub-trochanteric level, a base located at the trans-trochanteric level and a central axis aligned with the axis of the femoral neck, all in the aim of reorienting at a given degree the femoral head in the acetabulum in a rotational fashion depending on the need of the patient, so as to transfer an ill zone in said femoral head from a weight bearing zone to a non-weight bearing zone, said instrument comprising:

a) a cutting guide attachable to a hollowed cervical screw previously inserted into the femoral head along the central axis of the cone to be cut, said guide, once fastened, being free to rotate relative to said cervical screw around the axis of said cervical screw;

b) a drilling bit passing through said guide in an oblique hole having a slope which corresponds to half the angle of the cone to be cut, in order to penetrate the bone at the level of the lateral wall of the femur as close as possible to said cervical screw and thus cut the cone by lateral displacement of the bit in a circular motion which is progressively enlarged as the drill bit moves forward in the femur head, thus initiating cutting of the cone from its tip to its base; and c) means to connect the drill bit on the guide to drive it in rotation about its own axis, said means being also devised to allow the bit to be moved forward while it is rotated about the axis of the cervical screw, wherein said drill bit has a free end with a peripheral wall and appointed extremity that are very sharp and cutting, a base portion which allows said bit to be rigidly connected to said guide and to be driven in rotation, and a central portion with a surface that is smooth and non cutting.

21. An instrument, as defined in claim 20, wherein the middle portion of said drill bit is made of a flexible and resistant spring or cable.

22. An instrument, as defined in claim 21, wherein said middle portion of the drill bit is surrounded by a a slim and resistant protection guard.

23. An instrument, as defined in claim 22, wherein said protection guard includes one or more ball bearings.

24. An instrument, as defined in claim 20, wherein said middle portion of the drill bit is surrounded by a slim and resistant protection guard.

25. An instrument, as defined in claim 24, wherein said protection guard includes one or more ball bearings.

26. A surgical kit for use to make a cut shaped as a cone in the proximal femur of a patent, said cone having tip located on the postero lateral side at the sub-trochanteric level, a base located at the transtrochanteric level, and a central axis aligned with the axis of the femoral neck, all in the aim of reorienting rotationally at a given degree the femoral head in the acetabulum depending on the need of the patient, so as to allow displacement of a ill zone of the femoral head outside a weight bearing zone to a non weight bearing zone, said bit comprises, in combination:

a) a surgical instrument comprising
a cutting guide attachable to a hollowed cervical screw previously inserted into the femoral head along the central axis of the cone to be cut, said guide, once fastened, being free to rotate relative to said cervical screw around the axis of said cervical screw;

a drilling bit passing through said guide in an oblique hole having a slope which corresponds to half the angle of the cone to be cut, in order to penetrate the bone at the level of the lateral wall of the femur as close as possible to said cervical screw and thus cut the cone by lateral displacement of the bit in a circular motion which is progressively enlarged as the drill bit moves forward in the femur head, thus initiating cutting of the cone from its tip to its base; and means to connect the drill bit on the guide to drive it in rotation about its own axis, said means being also devised to allow the bit to be moved forward while it is rotated about the axis of the cervical screw;

b) a chisel insertable into the cervical screw, said chisel having a distal extremity from which projects a plurality of cutting wings oriented at angle with respect to each other;

c) a compression plate insertable in said cervical screw after the cone has entirely been cut and after said surgical instrument has been removed, said plate having a proximal extremity provided with the same number of blades as the number of wings of the chisel, said blades being insertable in the slits left in the bone by said cutting wings of said chisel, said proximal extremity being provided with a central hole sized to fit into the distal extremity of said cervical screw, and means allowing it to be fastened to the patient's femur;

d) a compression screw insertable in the said compression plate, and attachable to said centrally cervical screw; and e) a stabilizing hook member attachable to the greater trochanter and reattachable by compression to said compression plate.

27. A surgical kit as defined in claim 26, wherein said compression plate has means to allow said stabilizing hook member to be fastened to said compression plate.

28. A surgical kit as defined in claim 27, wherein said stabilizing hook member includes an end part supporting two rigid hooks, two flexible metallic cables which project from said rigid hooks, a cable coupling plate, and two threaded screws which extend from said metallic cables.

* * * * *